United States Patent [19]

Cook

[11] Patent Number: 4,474,046
[45] Date of Patent: Oct. 2, 1984

[54] ROD BENDER

[75] Inventor: Everett J. Cook, North Manchester, Ind.

[73] Assignee: Zimmer, Inc., Warsaw, Ind.

[21] Appl. No.: 389,648

[22] Filed: Jun. 18, 1982

[51] Int. Cl.³ .............................................. B21D 7/06
[52] U.S. Cl. ........................................ 72/409; 72/413; 72/477; 81/416
[58] Field of Search ............... 72/409, 388, 387, 482, 72/481, 480, 158, 219, 321, 413, 477; 140/102.5, 140/106; 81/416, 308, 304

[56] References Cited

U.S. PATENT DOCUMENTS

| 124,362 | 3/1872 | Kernon . | |
|---|---|---|---|
| 811,516 | 1/1906 | Mull | 72/158 |
| 1,042,112 | 10/1912 | Hartman | 72/388 |
| 1,479,762 | 1/1924 | Wagenbach | 72/388 |
| 2,087,125 | 7/1937 | Smith et al. | 140/106 |
| 2,502,713 | 4/1950 | Fagge | 72/388 |
| 3,610,019 | 10/1971 | Denninger | 72/413 |
| 3,709,264 | 1/1973 | Amman | 140/106 |
| 3,824,834 | 7/1974 | Durham | 72/387 |
| 3,901,064 | 8/1975 | Jacobson | 72/219 |
| 4,091,845 | 5/1978 | Johnson | 140/106 |
| 4,132,100 | 1/1979 | Schuler | 72/217 |
| 4,304,117 | 12/1981 | Rawson | 72/388 |

FOREIGN PATENT DOCUMENTS

| 177466 | 11/1907 | Fed. Rep. of Germany | 72/387 |
|---|---|---|---|
| 511864 | 1/1921 | France | 72/388 |
| 15345 | of 1911 | United Kingdom | 72/387 |
| 126994 | 5/1919 | United Kingdom | 140/102.5 |

*Primary Examiner*—Daniel C. Crane
*Attorney, Agent, or Firm*—Margaret L. Geringer

[57] ABSTRACT

An instrument for bending and/or contouring a rod. The device has a fulcrum for bending which has a plurality of separate bending surfaces, each of which can be rotated into operating position to accommodate different sizes of rods or to provide for different severities of bend.

7 Claims, 19 Drawing Figures

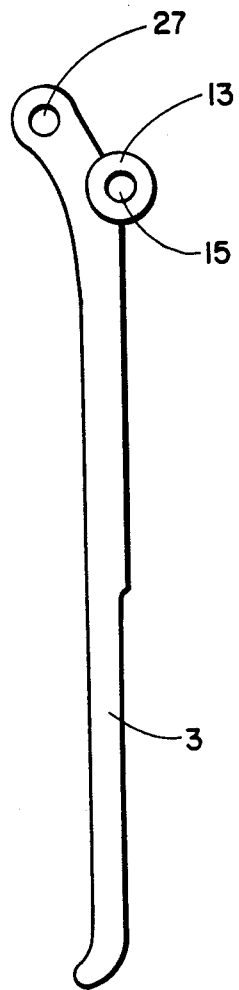
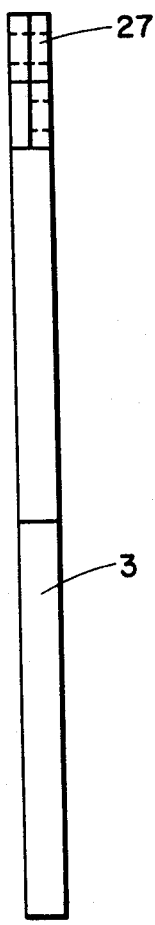
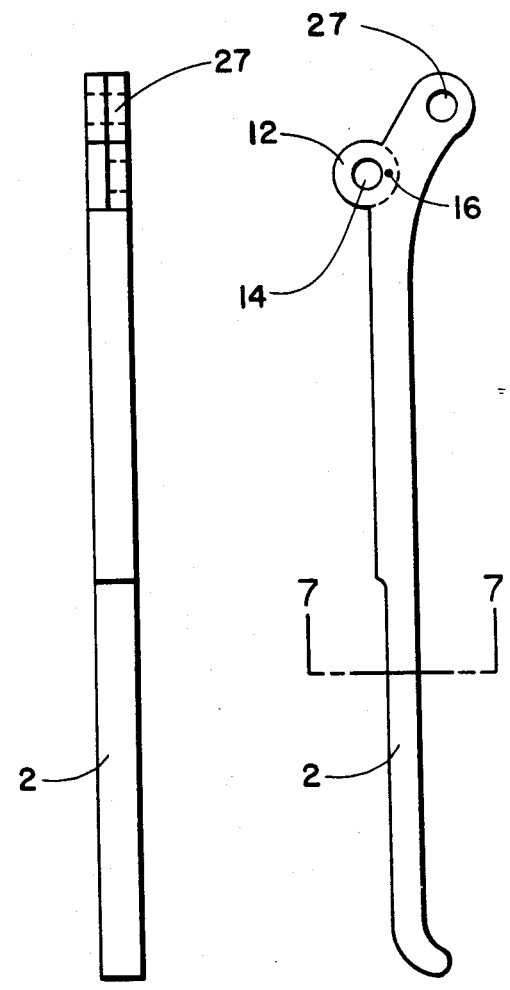
FIG. 5a.  FIG. 5b.  FIG. 6a.  FIG. 6b.
FIG. 7

ROD BENDER

BACKGROUND OF THE INVENTION

The present invention generally relates to instruments for bending rods.

A wide variety of instruments are known in the art for bending rods. One such style of device utilizes a three-post bending combination in association with a handle or lever combination. In such a device the center post is generally located at the pivot of the two-arm device and each of the two outer posts are mounted on an arm so as to be pivotable therewith about the center post. Application of manually applied force to the handles or lever mechanism generally causes the outer posts to orbit about the center post in such a manner as to bend a rod-like article positioned between the center post and the outer posts about the center post.

An example of a bending tool utilizing a three-post bending combination is described in U.S. Pat. No. 4,304,117 to Richard Rawson. Another example is embodied in the device known as a French Rod Bender. The latter is illustrated in FIG. 1.

The hinge pin (or center post) of both the French Rod Bender and the Bending Tool described in the Rawson patent, have only one surface available for bending rods.

OBJECTS OF THE INVENTION

A principle object of this invention is to provide a rod bending tool which incorporates a plurality of different bending surfaces which can be selectively positioned into the desired operating position in order to accommodate different size rods, as well as providing for varying severities or contours of bend to the rod.

Another object of the invention is to provide such a rod bending instrument which provides a practical and simple means of rotating and securing the various bending surfaces into working position.

A further object of the invention is to provide a rod bending instrument having a plurality of distinct bending surfaces in order to provide a more versatile rod-bending instrument.

A still further object of the invention is to provide such a rod-bending instrument which is suitable for medical applications, such as the bending of spinal rods.

SUMMARY OF THE INVENTION

The present invention accomplishes all of the above objects of invention. The present invention provides a rod bending instrument which incorporates a fulcrum for bending which has a plurality of separate bending surfaces, each of which can be rotated and locked into an operating position so as to accommodate different sizes of rods or to provide for different severities or contours of bend.

The rod bending instrument includes a pair of handle or lever arms having a common pivot. The instrument includes a three-post bending combination mounted in combination with said handle mechanism. The three-post combination includes a center protruding post and two outer side protruding posts. The center post is generally located at the pivot. The outer posts are affixed to each handle so as to be pivotable therewith about said center post. The device is opened by separating the handles so as to provide clearance between the center post and outer posts for receiving a rodlike article. Then, after a rod has been positioned between the center post and the two outer posts, application of manually applied force for closing the handles causes the outer posts to orbit about the center post. This force further causes the rod to bend about the center post.

The center post of the present invention incorporates a plurality of separate bending surfaces which can be selectively positioned and locked in place in order to locate the desired bending surface in its proper operating position. The plurality of bending surfaces enables the instrument to be utilized for bending different size rods as well as for providing varying severities or contours of bend to the rod.

In a particularly advantageous embodiment of the invention, the center post pivotally connects a right and left lever arm. The center post is rotatable independently from the arms and includes a locking means which selectively locks the center post in the desired position to one of the lever arms. Therefore, when the locking means is employed, upon movement of the arms, the center post moves in fixed relation to the lever arm to which it has been locked or secured, but it moves in a rotational relation to the other lever arm.

The center post can be selectively rotated to the desired bending surface. This feature enables the same instrument to be used to bend various diameter rods, as well as provides the ability to bend the rod with varying severity or varying contours, hence providing a much more versatile instrument than a rod bending tool which only has one bending surface or bending die contour.

BRIEF DESCRIPTION OF THE DRAWINGS

These features and objects of the invention, as well as others, will become apparent to those skilled in the art by referring to the accompanying drawings in which:

FIG. 5a is a front view of the left handle portion of the rod bender of FIG. 3;

FIG. 5b is a side view of the left handle portion of FIG. a;

FIG. 6a is a front view of the right handle portion of the rod bender of FIG. 3;

FIG. 6b is a side view of the right handle portion of FIG. 6a;

FIG. 7 is a cross-sectional view of the handle portion taken along lines 7—7 of FIG. 6b;

FIG. 8b is a side view of the rotating bearing of FIG. 8a;

FIG. 10b is a front view of the pin portion of FIG. 10a;

FIG. 11b is a side view of the center hinge pin of FIG. 11a;

DETAILED DESCRIPTION OF THE INVENTION

Figure 1:
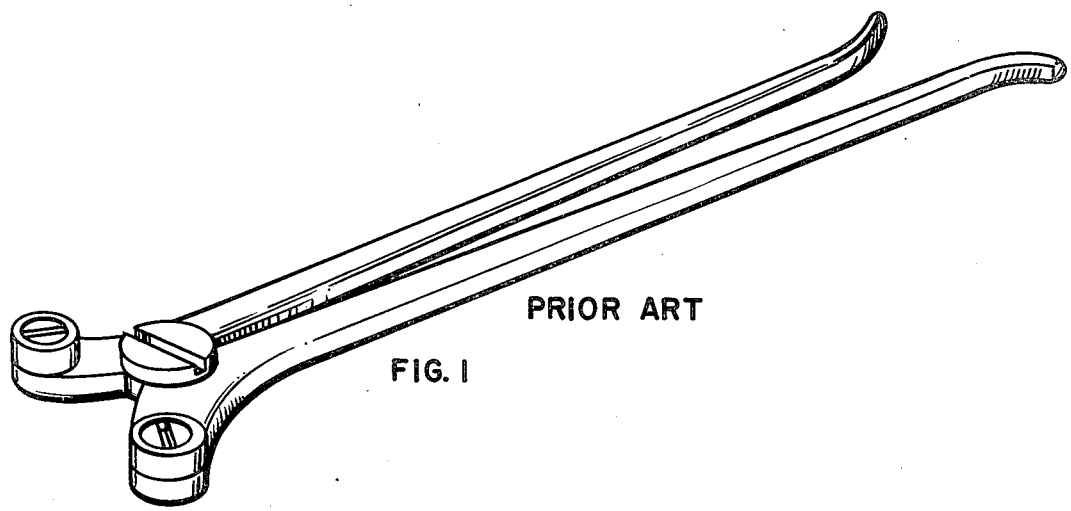
FIG. 1 is a pictorial view of a prior art French Rod Bender.
Figure 2:
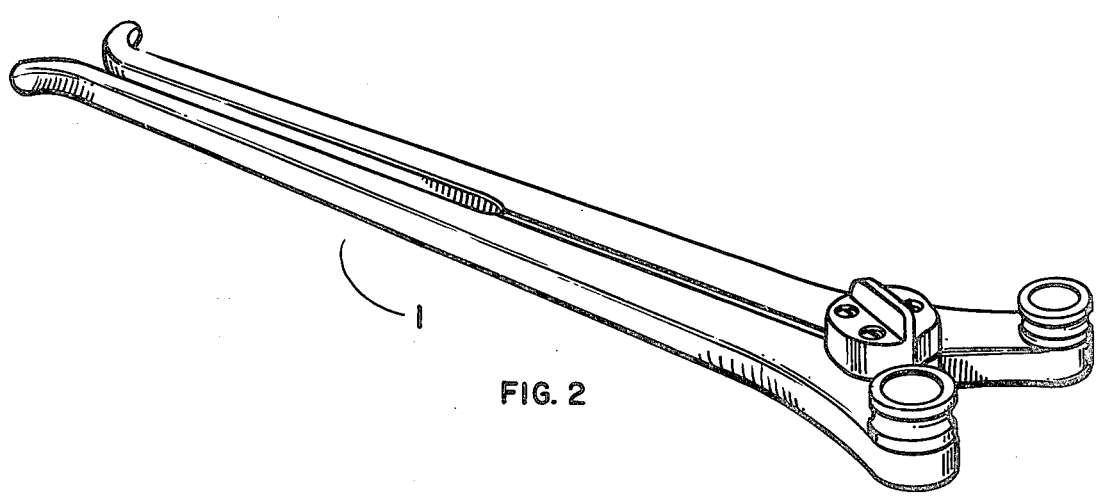
FIG. 2 is a pictorial view of a particular embodiment of the present invention.

FIGS. 2 through 13 illustrate a particularly advantageous embodiment of the rod bender according to this invention. The rod bender includes a pair of elongated opposing lever arms, a right lever 2 and a left lever 3. The two levers are joined together as shown by a common pivot 4. The gripping end 5 of the levers is on the proximal side of the pivot 4 and the rod contacting end 6 is located on the distal side of the pivot 4. The gripping end 5 of each lever arm is an elongated handle member.

The rod bender 1 is of the three post bending combination type. The three post bending combination includes a protruding center post 7 which is located at or mounted on the pivot area 4, and two protruding outer posts 8. One outer post 8 is located on the very distal tip of the right lever arm 2, and the other outer post 8 is located on the very distal tip of the left lever arm 3.

Figure 8A:
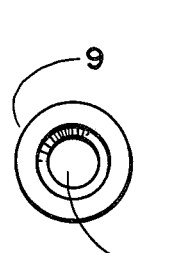
FIG. 8a is a front view of the rotating bearing of the outer posts of the rod bender of FIG. 3.
Figure 8B:
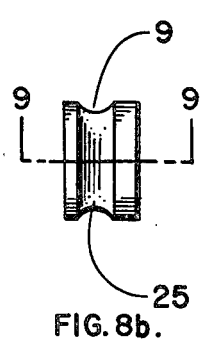
Figure 9:
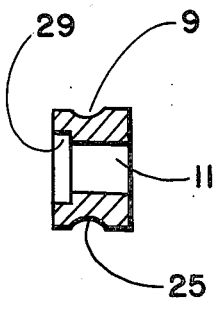
FIG. 9 is a cross-sectional view of the rotating-bearing taken along lines 9—9 of FIG. 8b.
Figure 10A:
FIG. 10a is a side view of the pin portion of the outer posts of the rod bender of FIG. 3.
Figure 10B:
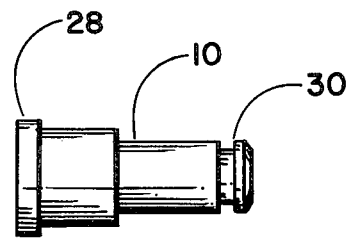

The outer posts of the present invention may be rotating bearings or rollers. The outer posts 8 are mounted on the distal tips of the lever arms 2 and 3. They are each comprised of a rotating outer bearing portion 9, as shown in FIGS. 8a, 8b, and 9. The rotating bearing 9 is substantially circular and includes hole 11 through the bearing 9. The outer posts 8 also include a pin 10 for securing the bearing 9 which is shown in FIGS. 10a and 10b.

Figure 12:
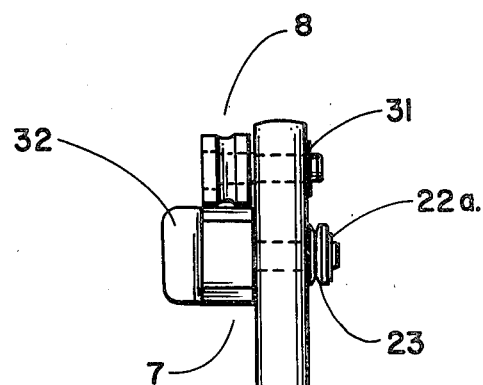
FIG. 12 is a side view of the assembled rod bender of FIG. 3.

Each lever arm includes a hole 27 as shown in FIGS. 5a and b and 6a and b. The pin 10 is inserted through the hole 11 of the bearing 9 and through the hole 27 in the lever arm. The pin includes a widened cylindrical portion 28 which rests in the widened hole portion 29 of the bearing 9. This prevents the pin 10 from slipping all the way through the hole 11. The pin 10 of the outer post 8 is then secured by a locking means, such as a C-ring 31 which locks into the grooved area 30 on the pin 10. The outer posts are thus secured to the lever arms with the bearing portion 9 protruding from the upper surface of the rod bending instrument, and the distal end of the pin 10 protruding from the bottom side with the C-ring 31 locking the pin 10 in place from the underneath side as shown in FIG. 12. Thus, the outer posts 8, are rotatable about the cylindrical pin portion 10. The bearing portion 9 may also include a groove 25 as shown in FIGS. 8b and 9. The groove 25 helps hold the rod that is to be bent in place.

Figure 11A:
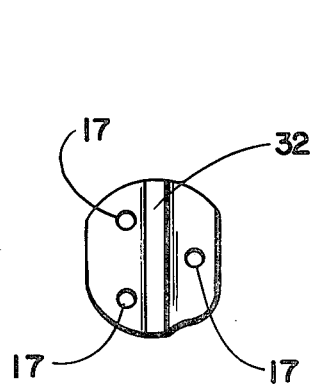
FIG. 11a is a front view of the center hinge pin (or center post) of the rod bender of FIG. 3.
Figure 11B:
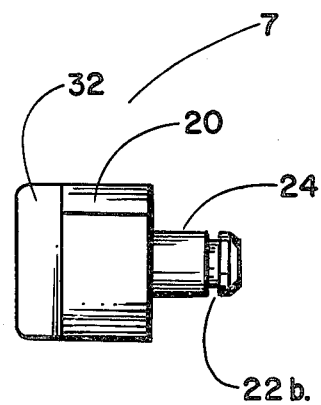

The center bending post 7 (as shown in FIGS. 11a and 11b) also acts as the hinge between the two lever arms 2 and 3. The right lever 2 has a protruding pivot portion 12 and the left lever 3 has a protruding pivot portion 13 as shown in FIGS 6b and 5b, respectively. The protruding portions 12 and 13 each have a hole 14 and 15, respectively. The center post 7 is comprised of an enlarged portion 20 and a thinner cylindrical hinge pin portion 24. Upon assembly of the lever arms 2 and 3, the two protruding portions 12 and 13, are aligned so that the two portions 12 and 13 are one on top of the other which line up the holes 14 and 15. The protruding portions 12 and 13 are each only half as thick as the lever arms 2 and 3, with one of the protruding portions extending from the bottom surface of its lever and the other extending from the top surface of its lever. When the portions 12 and 13 are aligned on top of each other, they form a thickness substantially equal to the thickness of the rest of the lever arm.

The thinner hinge portion 24 of the center post 7 is then inserted through the aligned holes 14 and 15, such that the lower surface 60 of the upper protruding post portion 20 rests on the upper surface of the top pivot portion. (In the embodiment illustrated, the pivot portion 12 of the right lever 2 is the uppermost pivot portion although it could be designed with either portion 12 or 13 as the upper portion.) The thinner hinge pin portion 24 slightly protrudes from the underneath side of the instrument 1 as shown in FIG. 12. A means is provided for securing the center post 7 to a lever arm. While it is understood that any suitable securing means may be used, the embodiment illustrated includes a thin groove 22b (as shown in FIG. 11b) on the portion of hinge pin 24 that protrudes from the underneath side of the levers. A locking ring such as a C-ring 22a locks into the groove 22b.

Figure 3:
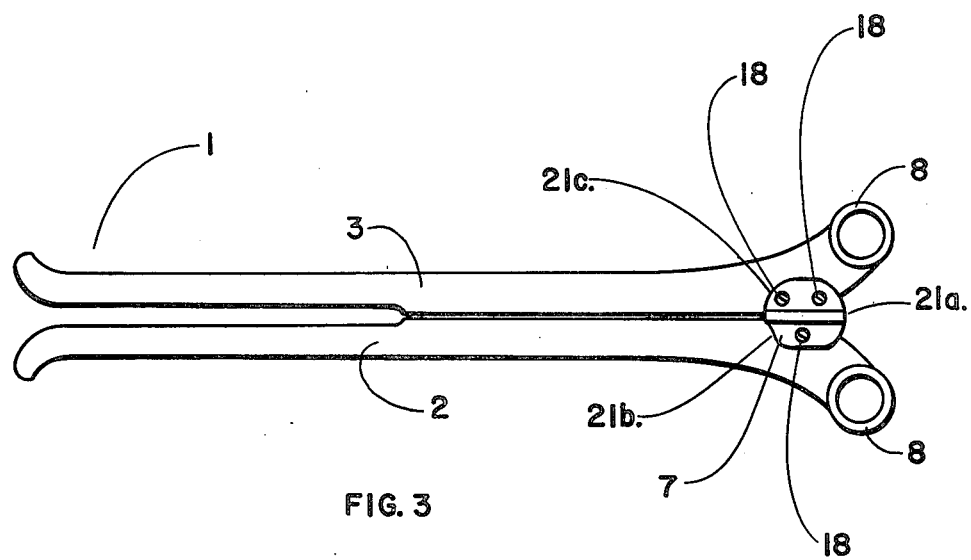
FIG. 3 is a front view of the rod bender of FIG. 2 in a closed position.
Figure 4:
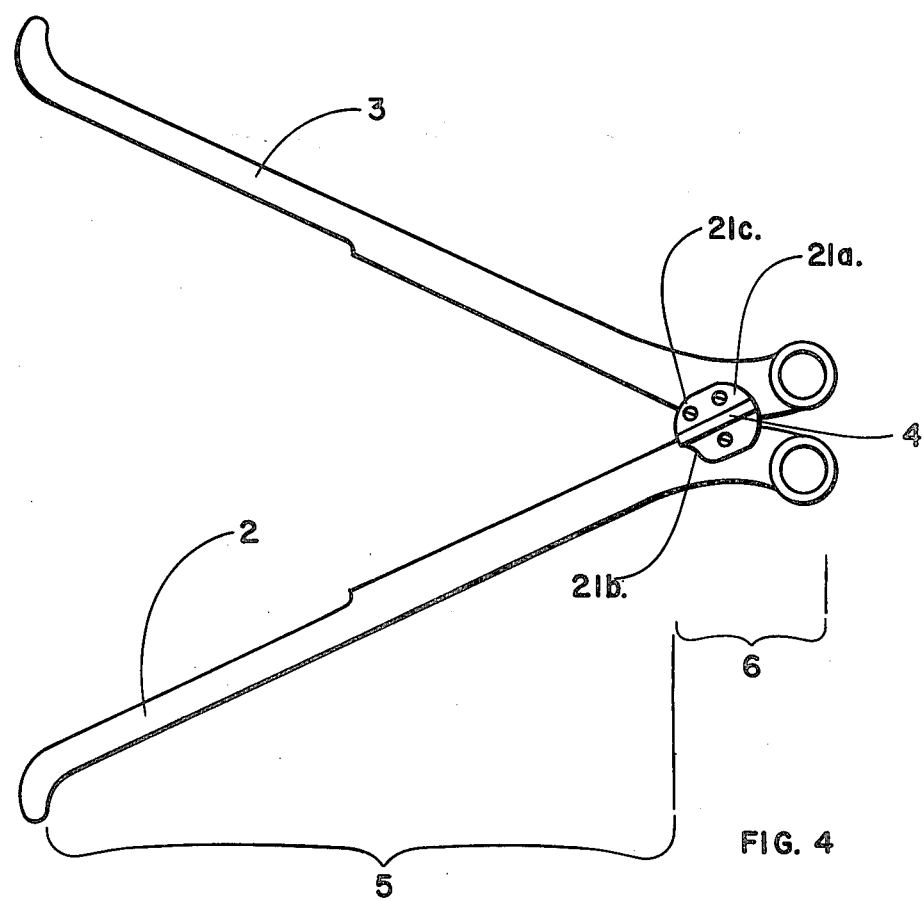
FIG. 4 is a front view of the rod bender of FIG. 3 in an open position.

The upper protruding portion 20 of the center post 7 includes a plurality of bending surfaces 21 (see FIGS. 3 and 4). Other conventional rod bending tools utilizes only a single bending surface contour. The present invention includes at least two or more different bending surface contours. The embodiment illustrated includes three distinct bending surface contours 21a, 21b, and 21c. Each bending surface 21 can be selectively positioned into the desired operating position. The variety of bending surface contours 21 enables the rod bender to accommodate different size rods, as well as provides for varying severities or contours of bend to the rod.

The center post may use any suitable means of selectively positioning the various bending surfaces 21 into operating position. Referring to FIGS. 6b, 11a and b, and 14, a particularly advantageous means is to use a locking means disposed between the under surface 60 of the enlarged protruding portion 20 and the upper surface of the uppermost pivot portion (12, in the embodiment illustrated). The locking means is comprised of a plurality of protrusions on one of these surfaces and a single mating indentation on the other interfacing surface. Each protrusion corresponds to a particular bending surface 21. The center post 7 can then be selectively rotated to cause the protrusion corresponding to the desired bending surface 21 to mate with the indentation, hence selectively positioning and securing the desired bending surface in operating position.

Alternatively, a plurality of indentations could be used with a single protruding portion for selectively engaging the indentations.

It can readily be seen that this system can be varied while still achieving a simple means of selectively locking in the desired bending surface 21 without interferring with the rotating action of the hinge.

In the embodiment illustrated, there are three bending surfaces 21a, b, and c. Three corresponding protrusions from the bottom surface 60 of the enlarged post portion 20 are utilized, with each protrusion corresponding to a particular bending surface. The appropriate protrusion mates with a single-indentation or depression 16 in the upper surface of the pivot portion 12 of lever 2 (See FIG. 6b).

Figure 13:
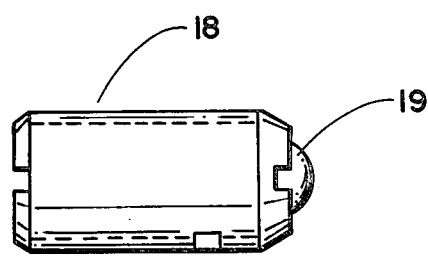
FIG. 13 is an enlarged side view of a ball plunger.

A convenient mechanism such as a spring plunger or ball plunger may be used to provide the protrusions. A suitable ball plunger is illustrated in FIG. 13. The ball plunger 18 has a cylindrical shape with external threads, as shown. A ball 19 protrudes from the bottom of the ball plunger 18. A spring (not shown) is located inside the ball plunger 18 such that in rest position, the spring causes the ball 19 to protrude from the ball plunger 18. (The plunger 18 is in rest position in FIG. 13, hence the ball 19 is protruding.) When pressure is applied to the ball, the spring compresses and the ball 19 recedes into the cylindrical portion of the ball plunger 18.

Figure 14:
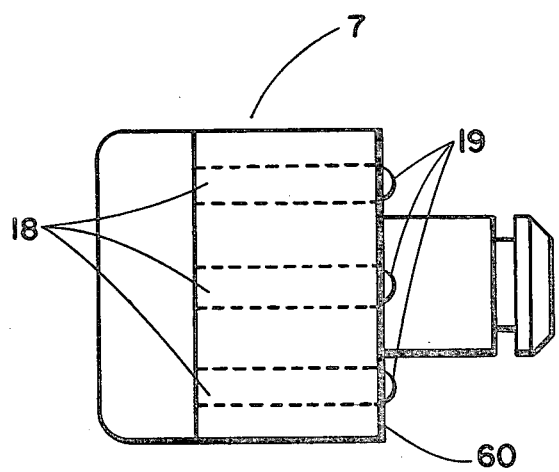
FIG. 14 is an enlarged view of the center post of FIG. 11b illustrating the ball plungers of FIG. 13 in position.

The enlarged center post portion 20 includes a threaded hole 17 (See FIG. 11a) for each ball plunger 18 to be threadedly inserted. The top of the ball plunger 18 has a suitable slot means for screwing the ball plungers 18 into the respective holes 17. Three ball plungers 18 are shown fully inserted into the enlarged post portion 20 of center post 7 in FIG. 14.

The ball plungers 18 (of FIGS. 13 and 14) and the indentation 16 (of FIG. 6b) are spaced so that each ball plunger 18 is able to selectively mate with the indentation 16 as the center post 7 is rotated. Each ball plunger 18 corresponds to a particular bending surface. The ball 19 of the ball plunger 18 which is selected to be in engagement with indentation 16 will protrude from the bottom surface 60 of the enlarged post portion 20 when positioned in alignment with indentation 16. Upon interengagement of the selected ball plunger 18, the bending surface 21 corresponding to the selected ball-plunger 18 will be operatively positioned for contacting a portion of the rod. Meanwhile, the balls 19 of the ball plungers 18 not in mating engagement with the indentation 16 are compressed up into the cylindrical portion of the ball plunger 18 by contact with surface 12.

A raised rib 32 (See FIGS. 11a and 11b) may be provided on the center post 7 to facilitate turning of the post 7 into the desired operating position.

Also, as shown in FIG. 12, an outer spring 23 may be utilized between the locking ring 22a and the bottom surface of the instrument 1. This spring 23 helps prevent the pivot 4 (or center post 7) interconnecting the two lever arms 2 and 3 from being too loose.

The center post 7 therefore serves a number of functions. First, it pins the two levers 2 and 3 together through a common pivot, allowing the handles or levers (2 and 3) to be rotated with respect to each other. Secondly, it provides a plurality of distinct bending surfaces which act as bending dies around which a rod may be bent. The center post illustrated includes three distinct bending surfaces. These three surfaces may each be at a different distance from the center of rotation. Each surface can be selectively rotated into working position by rotation of the center post causing the post 7 to selectively engage the upper most surface of the upper pivot portion of one of the levers.

The rod bender of the present invention is used as follows: The desired bending surface 21 is rotated and securely engaged into operating position; the operating position occuring when the selected surface of the center post faces toward the distal end of the instrument. The proximate end of the lever handles 2 and 3 are grasped with one handle in each hand and the handles are separated moderately. This causes the outer posts 8 to rotate in an arc upward and inward (in other words, the outer posts orbit about the center post) providing ample vertical clearance between the two outer posts 8 and the center post 7. With the ample clearance obtained, a suitable rod is then placed onto the selected bending surface 21 of center post 7 and under the two outer posts 8. A slight grip by the hands will bring the outer posts 8 down against the rod trapping it against the bending surface 21 of the center post 7. Additional force will bend the rod around the bending surface 21 of the center post. If a more or less severe bend is desired, this can be achieved by rotating the center post 7 to a different working surface or bending surface 21.

While this rod bending instrument can be used for bending any suitable rod, it is particularly helpful for use in bending spinal rods which are used in orthopaedic spinal surgery. These rods often have to be bent to varying contours during surgery. Also, there are various diameters of spinal rods that are used in this type of surgery, such as a 3/16" (4.8 mm) diameter spinal rod or a ¼" (6.4 mm) diameter spinal rod. The present invention enables the surgeon to need only one rod bending instrument in the operating room which is suitable for bending varying rod diameters as well as varying contours. This is a great advantage over the rod benders which include only a single bending surface. The present invention provides for a plurality of distinctly separate radial surfaces for bending rods, and includes a simple, but effective means of rotating the various surfaces into working position. As mentioned, this advantage provides the capability of bending two or more different sizes of spinal (or other) rods and provides at least two different severities of bend for each rod.

The invention described herein is a rod bending instrument incorporating a three post bending combination in which the center post includes a plurality of bending surfaces which can be selectively positioned into the desired operating position. Hence, this allows different size rods to be accommodated and bent with the instrument or allows the rod to be bent with varying severity or contours. While this invention has been described and exemplified in terms of a particularly advantageous embodiment, those skilled in the art can appreciate that modifications can be made without departing from the spirit and scope of this invention.

I claim:

1. An instrument for bending a rod comprising:
   a pair of pivotable elongaged opposing lever arms;
   a pivot interconnecting said lever arms intermediate their lengths so as to be pivotable thereabout, said pivot dividing said arms into a handle portion for opening and closing said arms and a bending portion operable by said handle portion; and
   a three-post bending assembly mounted on said bending portion, said assembly including a single center post mounted on said pivot and having a plurality of selectively lockable bending surfaces circumferentially spaced around the peripheral surface of said single center post for contacting a portion of the rod, and a pair of outer posts, one mounted on each of said arms and pivotable therewith, said center post being positioned relative to said pair of outer posts so as to define a channel therebetween for receiving said rod when said arms are open, said outer posts forcing said rod to bend about a selected bending surface when said arms are forcibly closed, said selected bending surface determining in part the shape of said bend.

2. An instrument for bending a rod as claimed in claim 1 wherein said center post is mounted on said pivot and is rotatable and lockable to one of said lever arms with said bending surfaces in a preselected position.

3. An instrument for bending a rod as claimed in claim 1 wherein said center post includes a raised rib for turning said center post and selectively positioning said bending surfaces.

4. An instrument for bending a rod as claimed in claim 2 wherein said center post includes a pivot shaft interconnecting said arms, said shaft having an enlarged protruding portion with said bending surfaces mounted therearound and further comprising locking means for selectively and releasably locking said bending surfaces located between the undersurface of the enlarged portion of the center post and the upper surface of the lever arm to which the center post is to be locked.

5. an instrument for bending a rod as claimed in claim 4 wherein said locking means includes a plurality of protrusions on one of said surfaces and a single mating indentation on said other surface wherein each said protrusion corresponds to a particular bending surface, and the center post can be selectively rotated to cause the protrusion corresponding to the desired bending surface to mate with the indentation and hence selectively positioning and securing in place the desired bending surface.

6. An instrument for bending a rod as claimed in claim 4 wherein said locking means includes a plurality of indentations on one of said surfaces and a single mating protrusion on said other surface wherein each said indentation corresponds to a particular bending surface, and the center post can be selectively rotated to cause the indentation corresponding to the desired bending surface to mate with the protrusion and hence selectively positioning and securing in place the desired bending surface.

7. An instrument for bending a rod comprising:
a pair of pivotable engaged opposing lever arms;
a pivot interconnecting said lever arms intermediate their lengths so as to be pivotable thereabout, said pivot substantially dividing said arms into a handle portion for opening and closing said arms and a bending portion operable by said handle portion; and
a three-post bending assembly mounted on said bending portion, said assembly including a single center post mounted on said pivot and having a plurality of selectively lockable bending surfaces circumferentially spaced around the peripheral surface of said single center post for contacting a portion of the rod, and a pair of outer posts, one mounted on each of said arms and pivotable therewith, said center post being positioned relative to said pair of outer posts so as to define a channel therebetween for receiving said rod when said arms are in one position, said outer posts forcing said rod to bend about a selected bending surface when said arms are forcibly rotated about said pivot point to a second position, said selected bending surface determining in part the shape of said bend.

* * * * *